United States Patent [19]  
Price

[11] Patent Number: 4,587,968  
[45] Date of Patent: May 13, 1986

[54] ELECTRIC EMASCULATOR AND METHOD FOR CASTRATING

[76] Inventor: David R. Price, Alden, Kans. 67512

[21] Appl. No.: 591,064

[22] Filed: Mar. 19, 1984

[51] Int. Cl.⁴ .................. A61B 17/32; A61B 17/38
[52] U.S. Cl. ......................... 128/303.1; 128/306; 30/140; 219/230
[58] Field of Search ......... 128/303.1, 303.14, 303.17, 128/306; 30/140; 219/230

[56] References Cited
U.S. PATENT DOCUMENTS

| 1,062,146 | 5/1913 | Douglass | 128/306 |
| 3,117,578 | 1/1964 | Helbling | 30/140 X |
| 4,046,148 | 9/1977 | Meador | 128/303.1 |
| 4,516,574 | 5/1985 | Hewes, Jr. | 128/303.1 |

Primary Examiner—Lee S. Cohen  
Attorney, Agent, or Firm—John H. Widdowson

[57] ABSTRACT

An electric emasculator for castrating a bull calf or the like having a first scissor member pivotally connected to a second scissor member. The second scissor member has a structure defining a bifurcated fork with a pair of parallel upper edges. A heating element is positioned along one of the parallel upper edges to cauterize as an incident to the severing operation and assists in the blood coagulation to prevent the flow of blood and closure of blood vessels in the area of amputation. A method for castrating the bull calf includes registering the end of an arcuate-L shaped hook of the first scissor member with the bottom structure of the bifurcated fork simultaneously to lodging a crushing block, that is integrally bound to the first scissor member, against the top of a second cutting edge. The method additionally comprises cauterizing the severed tissue therebetween as an incident to the severing operation by releasing and conducting electricity to the heating element in order to assist in the blood coagulation to prevent the flow of blood and closure of blood vessels in the area of amputation.

2 Claims, 8 Drawing Figures

ELECTRIC EMASCULATOR AND METHOD FOR CASTRATING

BACKGROUND OF THE INVENTION

1. Field of the Invention

This invention provides an electric emasculator and means for castrating a bull calf. More specifically, this invention contemplates a novel electric emasculator and a means for castrating a bull calf, or the like, which employs the use of a crushing block which lodges on top of a bifurcated fork structure.

2. Description of the Prior Art

U.S. Pat. No. 1,456,639 by Lagier discloses a cutting shears having an electrically heated blade which is used for docking of animals as well as for cuttings the ears of certain breeds of dogs. U.S. Pat. No. 4,046,148 by Meador Illustrates an instrument for cutting navel cords and tails wherein the blade is heated so that cauterization occurs when the cut is made. U.S. Pat. No. 3,117,578 by Helbling relates to a docking iron which simultaneously cuts and cauterizes the stub of the animal's tail, coagulating the blood during the amputation. None of the foregoing prior art teaches or suggests the particular electric emasculator and method for castrating a bull calf, or the like, of this invention.

SUMMARY OF THE INVENTION

This invention accomplishes its desired objects by providing a novel electric emasculator for castrating a bull calf, or the like, which includes a first scissor member having a first shank and terminating at one end into a first structure defining an essentially arcuate-L shaped hook including a first cutting edge means in order to hook the scrotum of the bull calf, or the like, and assist in the severing operation. A second scissor member terminates at one end into a second structure defining a bifurcated fork with a pair of parallel upper edges and a bifurcated second shank. The first shank of the first scissor member pivotably lodges in the bifurcated second shank as the arcuate-L shaped hook including a first cutting edge means pivotally moves through the bifurcated opening between the bifurcated fork. One of the parallel upper edges has a structure defining a second cutting edge means. A heating element means is positioned along the other parallel upper edge to cauterize as an incident to the severing operation and assist in blood coagulation to prevent the flow of blood and closure of blood vessels in the area of amputation. An electric conductor means is engaged to a power source for conducting electricity to the heating element means. The second scissor member has a structure defining a generally longitudinal conduit where through the electric conductor means lodges in its connection path to the heating element means. This invention also accomplishes its desired objects by providing a method for castrating a bull calf, or the like, comprising the steps of lodging the scrotum of the bull calf, or the like, in a receptacle zone defined by an arcuate-L shaped hook including a first cutting edge means and an integrally bound crushing block of a first scissor member and a bifurcated fork with a pair of parallel upper edges of a second scissor member wherein one of the parallel upper edges defines a second cutting edge and a heating element means is positioned along the other opposed parallel upper edge. The first cutting edge means of the arcuate-L shaped hook of the first scissor member is pivotally moved between the bifurcated fork of the second scissor member. The method for castrating additionally comprises registering the end of the arcuate-L shaped hook with the bottom of the structure of the bifurcated forks simultaneously to lodging the crushing block against the top of the second cutting edge means in order to sever the scrotum and testicles there between; and cauterizing the severed tissue there between as an incident to the severing operation by releasing and conducting electricity to the heating element means in order to assist in blood coagulation to prevent the flow of blood and the closure of blood vessels in the area of amputation.

It is an object of the invention to provide a novel electric emasculator which is capable of easily being operated.

Still further objects of the invention reside in the provision of an electric emasculator and method for castrating a bull calf, or the like.

These together with the various ancillary objects and features will become apparent as the following description proceeds, are attained by this invention, preferred embodiments being shown in the accompanying drawings, by way of example only, wherein:

DETAILED DESCRIPTION OF THE INVENTION

Figure 1:
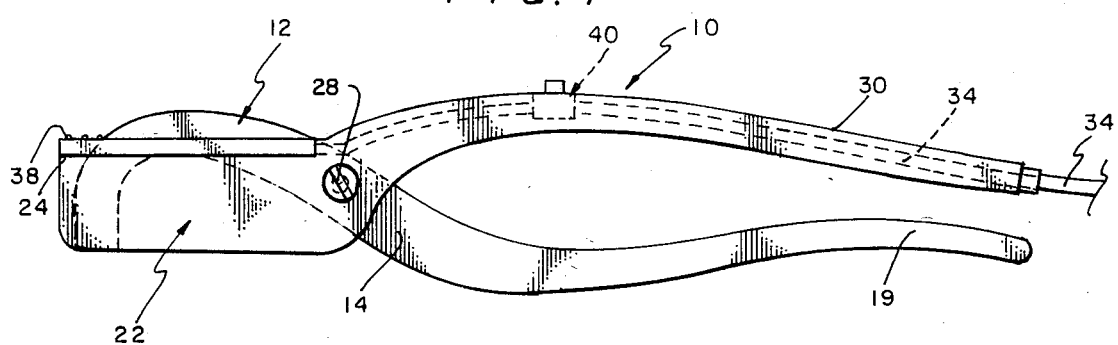
FIG. 1 is a side elevational view of the electric emasculator in the closed position.
Figure 2:
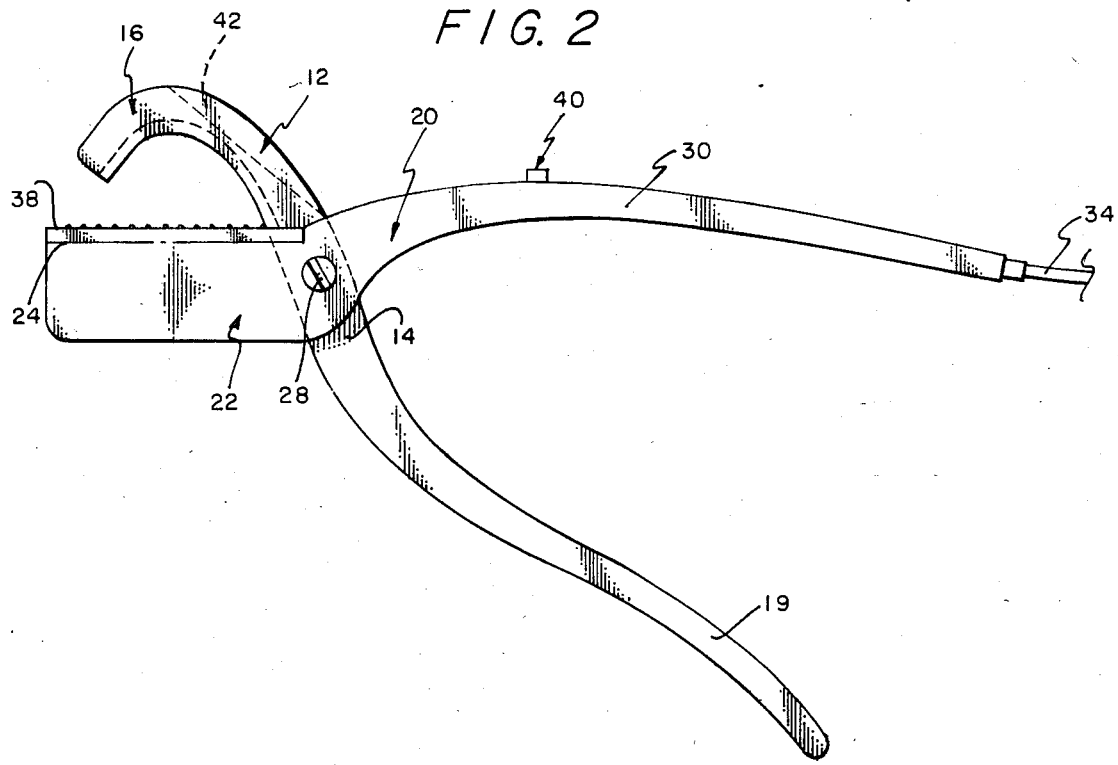
FIG. 2 is a side elevational view of the electric emasculator in an open position.

Referring in detail now to the drawings, wherein like reference numerals designate similar parts throughout the various views, there is seen an electric emasculator, generally illustrated as 10, for castrating a bull calf, or the like. The emasculator 10 includes a first scissor member, generally illustrated as 12, having a first shank 14 and terminating at one end into a structure defined by an essentially arcuate-L shaped hook, generally illustrated as 16, including a cutting edge 18 in order to hook the scrotum containing testicles of the bull calf, or the like, and to assist in the severing operation. First scissor member terminates at the other end into a handle 19.

Figure 7:
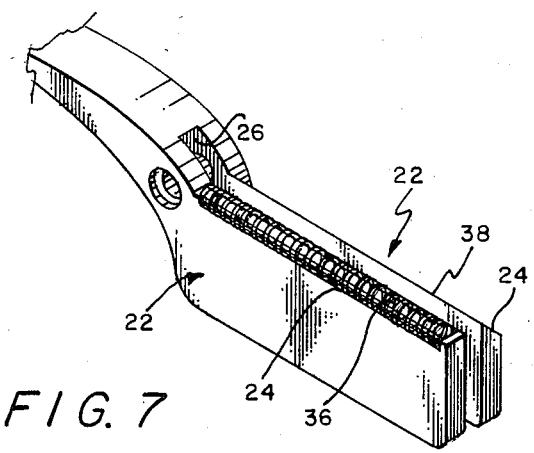
FIG. 7 is an exploded perspective view of the scissor member which includes an end defined by a bifurcated fork having one of the parallel upper edges defined as a cutting edge and a heating element positioned along the other opposed upper parallel edge.
Figure 8:
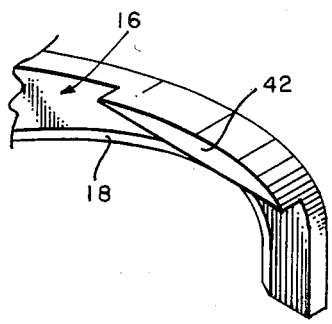
FIG. 8 is a partial enlarged perspective view of the arcuate-L shaped end of the other scissor member and depicting a crushing block integrally bound thereto.

A second scissor member, generally illustrated as 20, terminates at one end into a second structure defining a rectangular bifurcated fork, generally illustrated as 22, with a pair of parallel upper edges 24—24 and a bifurcated shank 26 (see FIG. 7). First shank 14 of member 12 pivotally lodges within the bifurcated second shank 26 as the arcuate-L shaped hook 16 with the first cutting edge 18 pivotally moves through the opening of the bifurcated fork 22 in the scissoring or severing action. A bolt 28 pierces the first shank 14 and the bifurcated second shank 26 to pivotally bound the first scissor member 12 and second scissor member 20 together. Scissor member 20 terminates at the other end into a second handle 30 that has a structure defining a generally longitudinal conduit 32 (see FIG. 4) wherethrough an electric conductor 34 lodges in its connection path to a heating element 36 that is positioned along one of the parallel upper edges 24 of the rectangular bifurcated fork 22. The other parallel upper edge 24 has a structure defining a second cutting edge 38. The heating element 36 functions to cauterize as an incident to the severing operation and assist in blood coagulation to prevent the flow of blood and closure of blood vessels in the area of amputation. The first cutting edge 18 and the second cutting edge 38 slidably contact each other when the emasculator 10 is in a closed docking position (see FIG. 5). This is important for a clean smooth sever and to facilitate immediate cauterization with the heating element 36.

Figure 3:
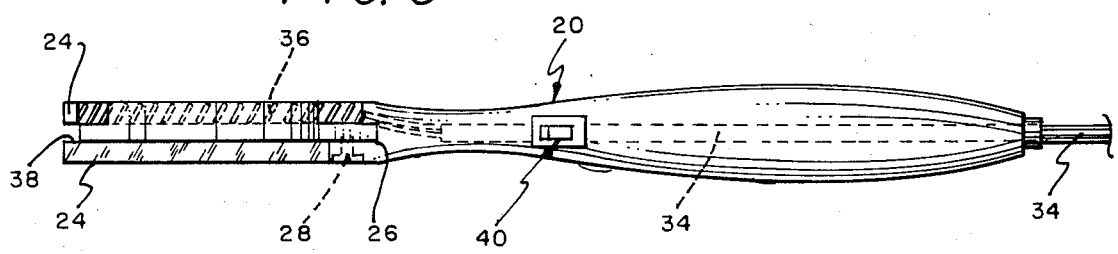
FIG. 3 is a top plan view of the scissor member which includes the heating element.
Figure 6:
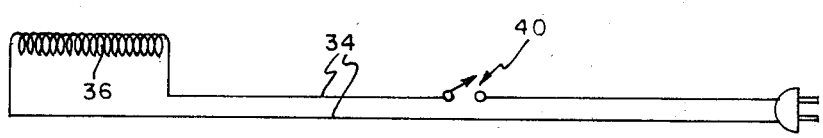
FIG. 6 is an electrical diagram of the circuit for the electric emasculator.

The electric conductor 34 is engaged to a power source (see FIG. 6) for conducting electricity to the element 36. The handle 30 terminates at a point (see FIGS. 1, 3 and 4) where the electric conductor 34 enters into the longitudinal conduit 32 of the handle 30.

A switch means, generally illustrated as 40, is situated on the second scissor member 20 and is in the electrical communication with the heating element 36 within electrical conductor 34 for releasing or cutting power to the heating element 36.

Figure 4:
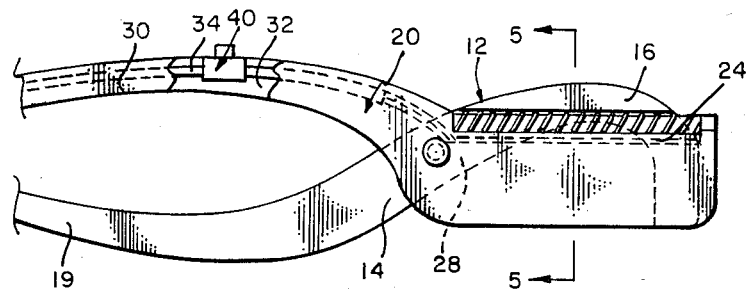
FIG. 4 is another side elevational view of the electric emasculator in which the electric conductor leading to the heating element represented by dotted lines.
Figure 5:
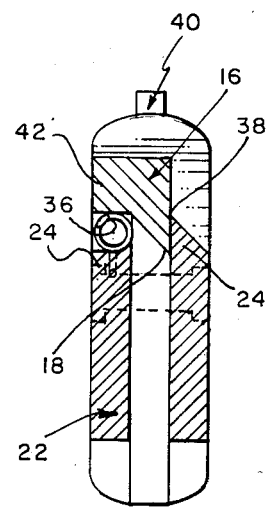
FIG. 5 is a vertical sectional view taken in direction of the arrows and along the plane of line 5—5 in FIG. 4.

An important feature of this invention is a crushing block 42 that is integrally bound to the essentially arcuate-L shaped hook 16 which functions to stop or limit the downward cutting movement of the first cutting edge 18 of the first scissor member 12 between the bifurcated fork 22 and as the cutting edge 18 and the cutting edge 38 slidably contact each other when the emasculator 10 is in a closed docking position as represented by FIG. 5. The crushing block 42 is integrally bound to the essentially arcuate-L shaped hook 16 at a point on same such that the end of the arcuate-L shaped hook 16 registers with the bottom of the rectangular bifurcated fork 22 as illustrated in FIGS. 1, 4 and 5.

With continuing reference to drawings for operation of the invention and the method for castrating a bull calf or the like, the scrotum (not shown in the drawings) of the bull calf containing the testicles hooked with the arcuate-L shaped hook 16 or is lodged between the opening or receptacle zone defined by the arcuate-L shaped hook 16 (including the integrally bound crushing block 42) of scissor member 12 and the bifurcated fork 22 of the scissor member 20. The handles 30 and 19 are subsequently compressed by the user towards each other causing the cutting edge 18 of the arcuate-L shaped hook 16 to slidably contact the cutting edge 38 and to move between the upper edges 24—24 of the bifurcated fork 22 of the scissor member 20. The handles 30 and 19 are continually depressed until the end of the arcuate-L shaped hook 16 registers with the bottom of the rectangular structure of the rectangular bifurcated fork 22 (as represented in FIGS. 1, 4 and 5) simultaneously to lodging or forcing the crushing block 42 against the top of the cutting edge 38 in order to cleanly, smoothly sever the lodged scrotum and testicles. The switch 40 is depressed to close the circuit (of FIG. 6) and conduct electricity to the heating element 36 which cauterizes any tissue that comes in contact with the heating element 36 in order to assist in blood coagulation to prevent the flow of blood and closure of blood vessels in the area of amputation.

Depending on the type of severing operation involved, switch 40 may be depressed before any tissue is severed, simultaneously to severing tissue, or subsequent to any tissue being severed. In a preferred embodiment to the invention, any tissue or cord to be cauterized is cauterized before or simultaneous to complete severing in order to prevent a loss of blood. This is a reason why an important feature of this invention is that cutting edge 38 be positioned on the opposed side or edge 24 (and not of the same side or edge 24) as that of the heating element 36 in order not to cut any tissue or cord before there is time to cauterize.

As was previously mentioned, another important feature of this invention is that cutting edge 18 and the cutting edge 38 slidably contact each other when the emasculator 10 is in the closed docking position of FIG. 5; this provides smooth severing of any tissue. The provision of the docking block 42 and the position of the same with respect to the heating element 36 and the cutting edges 18 and 38 is important to this invention; this provides for improved cauterization with heating element 36 and stops or limits the movement of cutting edge 18 between bifurcated edges 24—24 to protect the sharpness of cutting edge 38 by not allowing the same to engage the structure of the arcuate-L shaped hook 16 (see FIG. 5).

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. An electric emasculator for castrating a bull calf or the like comprising a first scissor member having a first shank and terminating at one end into a first structure dfining an essentially arcuate-L shaped hook including a first cutting edge means in order to hook the scrotum of the bull calf or the like and assist in the severing operation;

a second scissor member pivotally secured to said first scissor member and terminating at one end into a second structure defining a bifurcated fork with a pair of parallel upper edges and a bifurcated second shank, said first shank of said first scissor member pivotally lodges within said bifurcated second shank as said arcuate-L shaped hook including said first cutting edge means scissors through the bifurcated opening between the bifurcated fork;

one of said parallel upper edges has a structure defining a second cutting edge means;

a heating element means positioned entirely along the other parallel upper edge to cauterize as an incident to the severing operation and assist in blood coagulation to prevent the flow of blood and closure of blood vessels in the area of amputation;

an electric conductor means engaged to a power source for conducting electricity to the heating element means; said second scissor member having a structure defining a generally longitudinal conduit wherethrough said electric conductor means lodges in its connection path to the heating element means;

said first scissor member additionally comprises a crushing block means integrally bound to said essentially arcuate-L shaped hook which stops or limits the downward cutting movement of the first cutting edge means of the first scissor member between the bifurcated fork;

a switch means situated on said second scissor member for releasing power to the heating element means;

a bolt means piercing the first and second shank to pivotally bound the first scissor member and second scissor member together;

said crushing block means is bound to said essentially arcuate-L shaped hook at a point on same such that the end of the first structure registers with the bottom of said second structure;

said first scissor member and said second scissor member each terminate at the other end into a first handle and a second handle respectively; and said second handle includes said longitudinal conduit structure and terminates at a point where said electric conductor means enters into said longitudinal conduit structure, said first cutting edge means and said second cutting edge means slidably contact each other when said emasculator is in a closed docking posture.

2. A method for castrating a bull calf or the like comprising the steps of:

(a) lodging the scrotum of the bull calf or the like in a receptacle defined by an arcuate-L shaped hook including a first cutting edge and an integrally bound crushing block of a first scissor member, and a bifurcated fork with a pair of parallel upper edges of a second scissor member wherein one of the parallel upper edge defines a second cutting edge and a heating element is positioned entirely along the other opposed parallel upper edge of the bifurcated fork;

(b) moving the first cutting edge of the arcuate-L shaped hook of the first scissor member between the bifurcated fork of the second scissor member;

(c) registering the end of the arcuate-L shaped hook with the bottom of the structure of the bifurcated fork simultaneously to lodging the crushing block against the top of the second cutting edge in order to sever the scrotum and testicles therebetween; and (d) cauterizing simultaneously to said registering step (c) the tissue therebetween as an incident to the severing operation by releasing and conducting electricity to the heating element in order to assist in blood coagulation to prevent the flow of blood and closure of blood vessel in the area of amputation.

* * * * *